United States Patent [19]
Trimbo et al.

[11] Patent Number: 5,166,189
[45] Date of Patent: * Nov. 24, 1992

[54] ENTERAL DIET FOR PATIENTS WITH PULMONARY DISEASE

[75] Inventors: Susan L. Trimbo, Evanston; W. Bruce Rowe, Chicago, both of Ill.; M. Umberto Bracco, Vevey, Switzerland

[73] Assignee: Clintec Nutrition Co., Deerfield, Ill.

[*] Notice: The portion of the term of this patent subsequent to May 26, 2009 has been disclaimed.

[21] Appl. No.: 853,948

[22] Filed: Mar. 19, 1992

Related U.S. Application Data

[63] Continuation of Ser. No. 348,338, May 5, 1989, Pat. No. 5,116,819.

[51] Int. Cl.$^5$ ........................ A61K 31/00; A23C 11/02
[52] U.S. Cl. .............................................. 514/2; 514/21
[58] Field of Search ..................................... 514/2, 21

[56] References Cited

U.S. PATENT DOCUMENTS

| | | |
|---|---|---|
| 962,753 | 6/1910 | Fischer et al. |
| 1,027,844 | 5/1912 | Hoering. |
| 2,194,188 | 3/1936 | Supplee. |
| 2,937,974 | 5/1960 | Ferguson, Jr. |
| 3,698,912 | 10/1972 | Winitz. |
| 3,699,219 | 10/1972 | Carlson, Jr. |
| 3,873,720 | 3/1975 | Suzuki et al. |
| 3,920,838 | 11/1975 | Flatt et al. |
| 4,438,144 | 3/1984 | Blackburn. |
| 4,497,800 | 2/1985 | Larson et al. |
| 4,604,286 | 8/1986 | Kawajiri. |
| 4,670,268 | 6/1987 | Mahmoud. |
| 4,687,782 | 8/1987 | Brantman. |
| 4,690,820 | 9/1987 | Simko. |
| 4,711,953 | 12/1987 | Roger et al. |

FOREIGN PATENT DOCUMENTS

| | | |
|---|---|---|
| 0189160 | 7/1986 | European Pat. Off. |
| 0246747 | 11/1987 | European Pat. Off. |
| 0265772 | 5/1988 | European Pat. Off. |
| WO86/07262 | 12/1986 | PCT Int'l Appl. |

OTHER PUBLICATIONS

Goldstein, S., The Metabolic, Ventilatory and Functional Effects of Refeeding Malnourished Patients With Emphysema, Ph.D. Thesis, Columbia University.
Wilson, D., et al, Nutrition and Chronic Lung Disease, Am Rev Resp Dis 1985; 132: 1347-1365.
Henderson, W. Eicosanoids and Lung Inflammation, Am Rev Respir Dis 1987; 135: 1175-1185.
Ensure HN High Nitrogen Liquid Nitrogen, pp. 38–42.
Pulmocare Specialized Nutrition for Pulmonary Patients, pp. 68–74.

Primary Examiner—Merrell C. Cashion, Jr.
Assistant Examiner—Choon P. Koh
Attorney, Agent, or Firm—Hill, Van Santen, Steadman & Simpson

[57] ABSTRACT

An enteral diet for patients with pulmonary disease comprising not less than 18% of said calories from a high quality protein source; from about 20 to 50% of said calories from a slowly metabolizable carbohydrate source derived from maltodextrin or other partially hydrolyzed polysaccharides; from about 40–55% calories from a mixture of lipids comprising medium and long chain triglycerides.

21 Claims, No Drawings

ENTERAL DIET FOR PATIENTS WITH PULMONARY DISEASE

This is a continuation of application Ser. No. 348,338, filed May 5, 1989, now U.S. Pat. No. 5,116,819.

BACKGROUND OF THE INVENTION

1. Field of the Invention

The claimed subject matter pertains to an enteral diet, i.e. oral or tube feed for patients with pulmonary disease.

2. Description of the Related Art

Two products are currently available for nutritional therapy for pulmonary disease patients. Pulmocare TM (Ross Laboratories), a high fat product, contains 16.7% (62.6 g/l) protein, 55.2% (92.1 g/l) fat, and 28.1% (105.7 g/l) carbohydrates. The sources of these macronutrients are casein, corn oil, and sucrose and hydrolyzed cornstarch, respectively. Ensure HN TM (Ross Laboratories) contains 16.7% (44.4 g/l) protein, 30.1% (35.5 g/l) fat, and 53.2% (141.2 g/l) carbohydrate. The sources of these macronutrients are casein and soy isolate, corn syrup and sucrose, and corn oil.

Researchers have studied the effects of short term enteral feeding on pulmonary patients. In particular, it has been found that nitrogen balance and muscle strength are improved in patients receiving either of two—Pulmocare TM (high fat) or Ensure HN TM (high carbohydrate). Dr. Goldstein, "The Metabolic Ventilatory and Functional Effects of Refeeding Malnourished Patients with Emphysema", dissertation, Columbia University.

Dr. Goldstein's work suggests that feeding with the high fat product, Pulmocare TM, is preferable if one wishes to reduce ventilatory response. This study suggests that respiratory patients (primarily emphysema and COPD patients) are hypermetabolic with the unique characteristic of being unable to tolerate the large carbon dioxide loads associated with metabolism of carbohydrates. Thus, the increases caloric requirements of these patients must be fulfilled with lipid rather than carbohydrate. This aspect of these patients' metabolic requirements has been addressed in the formulation of Pulmocare TM.

There are specific metabolic requirements, however, that are not met by Pulmocare TM. A large part of the increased caloric requirement is associated with supporting the respiratory musculature and the work requirement to maintain the blood gases within normal physiologic limits. This is especially true with even the minor increase in exercise associated with normal daily activities. There is a specific need for a calorie source that is readily available to the respiratory muscle and a source of high quality protein to support and maintain muscle structure and function. There may also be specific micronutrient requirements.

SUMMARY OF THE INVENTION

This invention relates to an enteral diet for patients with pulmonary disease. During mild exercise, ventilatory response as described by carbon dioxide production ($VCO_2$), minute ventilation (Ve), and arterial carbon dioxide oxygen tension ($PaCO_2$) is elevated in patients consuming the high carbohydrate formula compared with patients consuming a high fat formula. Increased ventilatory response is considered clinically detrimental in most patients with chronic lung disease. More $CO_2$ is generated per kilocalorie by the metabolism of carbohydrate compared to fat. Increased $CO_2$ production in turn increases ventilatory response. To meet the needs of patients with pulmonary disease a micronutrient composition of protein, carbohydrate, and lipid has been devised. Similarly, the composition of the enteral diet is adjusted so that essential amino acids, essential fatty acids, vitamins, minerals, and trace elements is designed to meet specific nutritional needs. In particular, the diet contains no less than about 18% protein derived from a high quality protein source, from about 20–50% carbohydrate derived from maltodextrin or other partially hydrolyzed polysaccharides, and from about 40–55% fat derived from soy, canola, olive oil, plus medium-chain triglycerides.

DETAILED DESCRIPTION OF THE INVENTION—BEST MODE

Because pulmonary patients have compromised lung function, elimination of carbon dioxide may be problematic. An ideal dietary formulation for pulmonary patients attempts to reduce carbon dioxide generation from dietary sources, hence minimizing the pulmonary burden. The proposed formula will contain primarily maltodextrins or other polysaccharides and will comprise 20 to 50% of total calories. The only commercially available pulmonary formula on the market contains a large amount of sucrose (54% of total carbohydrates from sucrose). In the present application, not more than one-third of the carbohydrate content will be from sucrose or other rapidly metabolizable sugar.

In chronic lung disease, lipid serves as preferred fuel. Medium chain triglycerides (MCT) are an ideal dietary lipid source because they are more readily absorbed, a useful feature in view of coexisting malaborptive disorders that have been reported in pulmonary patients. Ketones produced during the metabolism of MCT may be utilized by muscle tissue as an energy source. In the present formulation long-chain triglycerides (LCT) are provided as soy oil, canola or olive oil. These oils not only provide linoleic acid, an essential fatty acid, but also provide n-3 fatty acids. Linolic acid, the predominant n-3 fatty acid supplied by these oils, may serve as a precursor to other n-3 fatty acids which have anti-inflammatory activity. In the proposed formulation, lipid will comprise 40 to 50% of the total calories. MCT will comprise 25 to 70% of the total triglycerides in this formulation.

The formulation of this invention contains whey protein as the major protein source. Whey protein is a high quality protein containing 18% more essential amino acids and more branched chain amino acids than casein, the protein source in the existing pulmonary formula. Branched chain amino acids are preferentially oxidized by the diaphragm and may improve nitrogen retention in respiratory muscles. The formulation will contain no less than 18% of the calories as protein.

The formulation described here will also contain 100% of the USRDA in 1500 kilocalories of all vitamins and minerals with the exception of phosphorus. Phosphorus levels will exceed the recommendations to correct the hypophosphatemia reported in patients with lung disease.

A biologically compatible, nutritious surfactant, such as egg yolk phospholipids, soy phospholipids, or milk phospholipids is preferred over such surfactants as carrageenan. Christie et al, *Phospholipids in milk and diary products*, 40 J. Soc Dairy Tech. 10–12 (1987).

Other sources of triglycerides and fatty acids may be employed singly or in mixtures.

EXAMPLE I

The components listed on the Table A page are to be combined using the appropriate mixing technology in the amounts described to produce a 1-liter unit having an energy content of 1.2 kcal/ml. Water may be added as needed to give the final volume. The example shall not limit the invention to the formulation listed as modifications in keeping with the invention may be necessary for commercialization.

The formulation described in Example I is intended for patients with compromised lung function. The formulation may be fed by mouth or tube and may be used as a supplement or as a complete diet.

In this example the carbohydrate content is 35.7%, protein 18.3%, and fat 45.8%.

TABLE A

| NUTRIENT | QUANTITY (per liter) |
|---|---|
| Protein | |
| Lactalbumin or a Combination of Lactalbumin and Casein | 55 g (18.3%) |
| Carbohydrate | |
| Maltodextrin | 107 g (35.7%) |
| Fat | |
| Medium-Chain Triglycerides and Soybean Oil (70:30) Lecithin | 61 g (45.8%) |
| Vitamins (100% USRDA/1500 kcal) | |
| Vitamin A (I.U.) | 4000 |
| Vitamin D (I.U.) | 320 |
| Vitamin E (I.U.) | 24 |
| Vitamin K (mcg) | 125* |
| Vitamin C (mg) | 48 |
| Thiamin (mg) | 1.2 |
| Riboflavin (mg) | 1.4 |
| Niacin (mg) | 16 |
| Vitamin $B_6$ (mg) | 1.6 |
| Folic Acid (mcg) | 320 |
| Pantothenic Acid (mg) | 8 |
| Vitamin $B_{12}$ (mcg) | 4.8 |
| Biotin (mcg) | 240 |
| Choline (mg) | 450* |
| Minerals and Electrolytes | |
| Sodium (mg) | 500* |
| Potassium (mg) | 1250* |
| Chloride (mg) | 1000* |
| Calcium (mg) | 800 |
| Phosphorus (mg) | 1200** |
| Magnesium (mg) | 320 |
| Iron (mg) | 14.4 |
| Iodine (mcg) | 120 |
| Copper (mg) | 80 |
| Zinc (mg) | 12 |
| Manganese (mg) | 2* |

*No USRDA established.
**150% of USRDA

EXAMPLE II

The components listed in Table B are combined using the procedure described in Example I.

TABLE B

| | Per liter of formula at 1.5 kcal/ml |
|---|---|
| Protein (g) | |
| Whey protein* (g) | 13.5 |
| Casein (g) | 54 |
| | 67.5 |
| Carbohydrate (g) | |
| Maltodextrin (g) | 71.3 |
| Sucrose (g) | 30.0 |

TABLE B-continued

| | Per liter of formula at 1.5 kcal/ml |
|---|---|
| | 101.3 |
| Fat (g) | |
| MCT (g) | 28.2 |
| Res. Milk Fat (g) | 22.1 |
| Lear Oil (g) | 39.6 |
| Lecithin (g) | 4.0 |
| | 93.9 |
| Vitamins | |
| Vitamin A (IU) | 7500 |
| Vitamin D (IU) | 420 |
| Vitamin E (IU) | 42 |
| Vitamin K (mcg) | 240 |
| Vitamin C (mg) | 210 |
| Thiamine ($B_1$) (mg) | 3 |
| Riboflavin ($B_2$) (mg) | 3.6 |
| Niacin (PP) (mg) | 42 |
| Vitamin $B_6$ (mg) | 6 |
| Folic Acid (mcg) | 810 |
| Pantothenic Acid (mg) | 21 |
| Vitamin $B_{12}$ (mcg) | 12 |
| Biotin (mcg) | 600 |
| Choline (mg) | 675 |
| Carnitine (mg) | 120 |
| Taurine (mg) | 120 |
| Minerals | |
| Sodium (mg) | 750 |
| Potassium (mg) | 1875 |
| Chloride (mg) | 1500 |
| Calcium (mg) | 1200 |
| Phosphorus (mg) | 2250 |
| Magnesium (mg) | 600 |
| Iron (mg) | 18 |
| Iodine (mcg) | 150 |
| Copper (mg) | 2.1 |
| Zinc (mg) | 21 |
| Manganese (mg) | 4.1 |
| Chromium (mcg) | 60 |
| Fluoride (mg) | 1.8 |
| Molybdenum (mcg) | 180 |
| Selenium (mcg) | 60 |

*From delactosed/decaseinated butter milk (40.9 g)

That which is claimed is:

1. A method for providing nutrition to a patient with pulmonary disease without increasing the ventilatory response of the patient comprising administering to a patient in need of same a sufficient amount of a composition having a calorie distribution which comprises:
    a) not less 18% of said calories from a high quality protein source;
    b) from about 20 to 50% of said calories from a carbohydrate source; and
    c) from about 40–55% of said calories from a mixture of lipids comprising medium and long chain triglycerides.

2. The method of claim 1 wherein the composition includes at least 100% of the USRDA of all vitamins and minerals.

3. The method of claim 1 wherein 20 to 70% of the total triglycerides are MCTs.

4. The method of claim 1 wherein said long chain triglycerides are selected from the group consisting of soy, canola, and olive oil.

5. The method of claim 1 wherein the composition includes a surfactant selected from the group consisting of egg yolk phospholipids, soy phospholipids and milk phospholipids.

6. The method of claim 1 wherein the carbohydrate source is a partially hydrolyzed polysaccharide.

7. The method of claim 1 wherein the composition includes phosphorus in amount greater than 100% USRDA.

8. A method of feeding patients with pulmonary disease without increasing ventilatory response comprising the step of:
enterally administering to a patient with pulmonary disease an effective amount of a composition comprising:
a protein source that constitutes not less than approximately 18% of the total caloric content of the composition;
a carbohydrate source; and
a mixture of medium and long chain triglycerides in an amount that constitutes at least approximately 40% of the total caloric content of the composition, 20 to 70% of the total triglycerides being MCTs.

9. The method of claim 8 wherein the composition includes at least 100% of the USRDA of all vitamins and minerals.

10. The method of claim 8 wherein the composition includes phosphorus at greater than 100% of the USRDA.

11. The method of claim 8 wherein long chain triglycerides are selected from the group consisting of soy, canola, and olive oil.

12. The method of claim 8 wherein the composition includes a surfactant selected from the group consisting of egg yolk phospholipids, soy phospholipids and milk phospholipids.

13. The method of claim 8 wherein said long chain triglycerides are selected from the group consisting of soy, canola, and olive oil.

14. A method for providing nutrition to a patient with pulmonary disease without increasing the ventilatory response of the patient comprising administering to a patient in need of same an effective amount of a composition which comprises:
a) a high quality protein source;
b) a carbohydrate source; and
c) a mixture of lipids comprising medium and long chain triglycerides, wherein 20 to 70% of the total triglycerides are MCTs.

15. The method of claim 14 wherein the protein comprises at least 18% of the calorie distribution of the composition.

16. The method of claim 14 wherein said long chain triglycerides are selected from the group consisting of soy, canola, and olive oil.

17. The method of claim 14 wherein the carbohydrate source comprises about 20 to about 50% of the calorie distribution of the composition.

18. The method of claim 14 wherein the composition includes at least 100% of the USRDA of all vitamins and minerals.

19. The method of claim 14 wherein the composition includes phosphorus at greater than 100% of the USRDA.

20. The method of claim 14 wherein the composition includes a surfactant selected from the group consisting of egg yolk phospholipids, soy phospholipids and milk phospholipids.

21. The method of claim 14 wherein the carbohydrate source is a partially hydrolyzed polysaccharide.

* * * * *